US00PP28264P2

(12) United States Plant Patent
Koning

(10) Patent No.: US PP28,264 P2
(45) Date of Patent: Aug. 8, 2017

(54) ***LAVANDULA* PLANT NAMED 'ANOUK DELUXE 1205'**

(50) Latin Name: *Lavandula stoechas*
Varietal Denomination: Anouk Deluxe 1205

(71) Applicant: Lammert Koning, Nuis (NL)

(72) Inventor: Lammert Koning, Nuis (NL)

(73) Assignee: L. KONING BEHEER B.V., Nuis (NL)

( * ) Notice: Subject to any disclaimer, the term of this patent is extended or adjusted under 35 U.S.C. 154(b) by 0 days.

(21) Appl. No.: 14/999,116

(22) Filed: Mar. 31, 2016

(51) Int. Cl.
*A01H 5/02* (2006.01)

(52) U.S. Cl.
USPC ..... Plt./445

(58) Field of Classification Search
USPC ..... Plt./445
See application file for complete search history.

*Primary Examiner* — Annette Para
(74) *Attorney, Agent, or Firm* — C. A. Whealy

(57) ABSTRACT

A new and distinct cultivar of *Lavandula* plant named 'Anouk Deluxe 1205', characterized by its broadly upright plant habit; freely branching growth habit; strong durable plants; freely flowering habit; violet to dark violet blue-colored flowers with numerous violet-colored terminal flower bracts positioned on strong and erect peduncles; strong re-flowering habit; and good garden performance.

2 Drawing Sheets

Botanical designation: *Lavandula stoechas.*
Cultivar denomination: 'ANOUK DELUXE 1205'.

BACKGROUND OF THE INVENTION

The present invention relates to a new and distinct *Lavandula* plant, botanically known as *Lavandula stoechas*, commonly referred to as Lavender and hereinafter referred to by the name 'Anouk Deluxe 1205'.

The new *Lavandula* plant is a product of a planned breeding program conducted by the Inventor in Boskoop, The Netherlands. The objective of the breeding program was to develop new unique *Lavandula* plants with good performance and attractive plant form and flower coloration.

The new *Lavandula* plant originated from a cross-pollination made by the Inventor in May, 2011 of *Lavandula stoechas* 'Anouk', disclosed in U.S. Plant Pat. No. 16,685, as the female, or seed, parent with *Lavandula stoechas* 'Sanne', disclosed in U.S. Plant Pat. No. 20,632, as the male, or pollen, parent. The new *Lavandula* plant was discovered and selected by the Inventor as a single flowering plant within the progeny of the stated cross-pollination in a controlled environment in Boskoop, The Netherlands in May, 2012.

Asexual reproduction of the new *Lavandula* plant by terminal cuttings in a controlled greenhouse environment in Boskoop, The Netherlands since August, 2012 has shown that the unique features of this new *Lavandula* plant are stable and reproduced true to type in successive generations.

SUMMARY OF THE INVENTION

Plants of the new *Lavandula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Lavandula* plant. These characteristics in combination distinguish 'Anouk Deluxe 1205' as a new and distinct *Lavandula* plant:

1. Broadly upright plant habit.
2. Freely branching growth habit.
3. Strong durable plants.
4. Freely flowering habit.
5. Violet to dark violet blue-colored flowers with numerous violet-colored terminal flower bracts positioned on strong and erect peduncles.
6. Strong re-flowering habit.
7. Good garden performance.

Plants of the new *Lavandula* differ primarily from plants of the female parent, 'Anouk', in the following characteristics:

1. Plants of the new *Lavandula* are more compact than plants of 'Anouk'.
2. Plants of the new *Lavandula* have a stronger re-flowering habit than plants of 'Anouk'.
3. Inflorescences of plants of the new *Lavandula* have more terminal flower bracts than inflorescences of plants of 'Anouk'.

Plants of the new *Lavandula* differ primarily from plants of the male parent, 'Sanne', in the following characteristics:

1. Plants of the new *Lavandula* have a stronger re-flowering habit than plants of 'Sanne'.
2. Inflorescences of plants of the new *Lavandula* have more terminal flower bracts than inflorescences of plants of 'Sanne'.

Plants of the new *Lavandula* can be compared to plants of the *Lavandula stoechas* 'Anouk Deluxe 173', disclosed in a U.S. Plant patent application Ser. No. 14/999,140. In side-by-side comparisons, plants of the new *Lavandula* differ primarily from plants of 'Anouk Deluxe 173' in the following characteristics:

1. Plants of the new *Lavandula* are more compact than plants of 'Anouk Deluxe 173'.
2. Inflorescences of plants of the new *Lavandula* have more terminal flower bracts than inflorescences of plants of 'Anouk Deluxe 173'.
3. Plants of the new *Lavandula* and 'Anouk Deluxe 173' differ in terminal flower bract color as plants of 'Anouk Deluxe 173' have purple violet-colored terminal flower bracts.

Plants of the new *Lavandula* can also be compared to plants of the *Lavandula stoechas* 'Toscane', disclosed in U.S. Plant Pat. No. 18,046. In side-by-side comparisons, plants of the new *Lavandula* differ primarily from plants of 'Toscane' in the following characteristics:

1. Plants of the new *Lavandula* are more compact than plants of 'Toscane'.
2. Plants of the new *Lavandula* have a stronger re-flowering habit than plants of 'Toscane'.
3. Inflorescences of plants of the new *Lavandula* have more terminal flower bracts than inflorescences of plants of 'Toscane'.

BRIEF DESCRIPTION OF THE PHOTOGRAPHS

The accompanying photographs illustrate the overall appearance of the new *Lavandula* plant showing the colors as true as it is reasonably possible to obtain in colored reproductions of this type. Colors in the photographs may differ slightly from the color values cited in the detailed botanical description which accurately describe the colors of the new *Lavandula* plant.

The photograph on the first sheet is a side perspective view of a typical flowering plant of 'Anouk Deluxe 1205' grown in a container.

The photograph on the second sheet is a close-up view of typical inflorescences of 'Anouk Deluxe 1205'.

DETAILED BOTANICAL DESCRIPTION

Plants used in the aforementioned photographs and following detailed description were grown in 12-cm containers during the spring and early summer in an outdoor nursery in Boskoop, The Netherlands and under cultural practices typical of commercial *Lavandula* production. Plants were ten months old when the photographs and description were taken. During the production of the plants, day temperatures ranged from 10° C. to 30° C. and night temperatures ranged from 5° C. to 20° C. In the following description, color references are made to The Royal Horticultural Society Colour Chart, 2007 Edition, except where general terms of ordinary dictionary significance are used.

Botanical classification: *Lavandula stoechas* 'Anouk Deluxe 1205'.

Parentage:

*Female, or seed, parent.*—*Lavandula stoechas* 'Anouk', disclosed in U.S. Plant Pat. No. 16,685.

*Male, or pollen, parent.*—*Lavandula stoechas* 'Sanne', disclosed in U.S. Plant Pat. No. 20,632.

Propagation:

*Type.*—Terminal vegetative cuttings.

*Time to initiate roots, summer and winter.*—About ten days at temperatures about 18° C.

*Time to produce a rooted young plant, summer.*—About 60 days at temperatures about 20° C.

*Time to produce a rooted young plant, winter.*—About 70 days at temperatures about 20° C.

*Root description.*—Fine, fibrous; initially white in color and becoming more brown with development; actual color of the roots is dependent on substrate composition, water quality, fertilizer type and formulation.

*Rooting habit.*—Freely branching; dense.

Plant description:

*Plant and growth habit.*—Herbaceous perennial; broadly upright plant habit; freely branching habit; moderately vigorous growth habit; flowers arranged in verticillasters on crowded spikes with numerous showy terminal flower bracts.

*Plant height, soil level to top of floral plane.*—About 36.4 cm.

*Plant width.*—About 34.5 cm.

*Lateral branch description.*—Quantity per plant: About 220 lateral branches developing per plant. Length: About 8.2 cm. Diameter: About 2 mm. Internode length: About 1.7 mm. Strength: Strong. Aspect: Upright to somewhat outwardly. Texture and luster: Densely tomentose; matte. Color: Close to 144B; pubescence, close to between 150D and 155A.

*Leaf description.*—Arrangement: Opposite, simple; sessile. Length: About 3.6 cm. Width: About 6 mm. Shape: Narrowly lanceolate. Apex: Acute. Base: Cuneate. Margin: Entire; revolute. Texture and luster, upper and lower surfaces: Moderately tomentose; matte. Fragrance: Strongly aromatic, pungent. Venation pattern: Pinnate. Color: Developing leaves, upper surface: Close to 191A. Developing leaves, lower surface: Close to 191B. Fully expanded leaves, upper surface: Close to 137B; venation, close to 146D; pubescence, close to 192D. Fully expanded leaves, lower surface: Close to 138B; venation, close to 138A; pubescence, close to 192D.

Flower description:

*Flower type, arrangement and habit.*—Small single salverform flowers arranged in compact verticillasters on crowded terminal spikes; freely flowering, about 180 flowers developing per inflorescence and more than 7,000 flowers developing per plant; flowers with two-lobed upper lip and three-lobed lower lip; flowers face mostly outwardly to slightly upright on the spike; inflorescences with numerous showy terminal flower bracts.

*Natural flowering season.*—Long flowering period; continuous from late spring into the summer in The Netherlands; strong re-flowering habit.

*Flower longevity on the plant.*—Individual flowers last about ten days on the plant; flowers not persistent.

*Fragrance.*—None detected.

*Flower buds.*—Length: About 6 mm. Diameter: About 2 mm. Shape: Narrowly oblong. Texture and luster: Moderately tomentose; matte. Color: Close to 145C; towards the apex, tinged with close to between N187B and 200C.

*Inflorescence height.*—About 5.8 cm.

*Inflorescence diameter, at terminal flower bracts.*—About 3.1 cm.

*Inflorescence diameter, below flower bracts.*—About 1.8 cm.

*Flower diameter.*—About 4 mm.

*Flower depth (height).*—About 8 mm.

*Petals.*—Quantity and arrangement: Upper lip, two-lobed and lower lip, three-lobed. Length, upper lip:

About 8 mm. Length, lower lip: About 7 mm. Width, upper lip: About 3 mm. Width, lower lip: About 4 mm. Shape: Roughly spatulate; lower 75% fused into a tube. Apex: Obtuse, rounded. Margin: Entire. Texture and luster, upper (inner) and lower (outer) surfaces: Smooth, glabrous, velvety; matte. Color: When opening, upper (inner) surface: Close to N92A; throat, close to 86A, towards the base, close to NN155D. When opening, lower (outer) surface: Close to N92A; tube, close to 86A, towards the base, close to NN155D. Fully opened, upper (inner) surface: Close to between 86A and N92A; throat, close to N81A, towards the base, close to NN155D; color does not fade with development. Fully opened, lower (outer) surface: Close to between 86A and N92A; tube, close to N81A, towards the base, close to NN155D; color does not fade with development.

*Terminal flower bracts*.—Quantity and arrangement: Numerous, about twelve positioned upright at inflorescence apex. Length: About 2.3 cm. Width: About 1 cm. Shape: Narrowly obovate. Apex: Obtuse. Base: Cuneate. Margin: Entire; slightly undulate. Texture and luster, upper and lower surfaces: Slightly tomentose (minute hairs); matte. Color, upper and lower surfaces: Close to 83B; pubescence, close to NN155D.

*Basal flower bracts*.—Quantity and arrangement: Each group of ten flowers is subtended by a single basal flower bract. Length: About 1 cm. Width: About 8 mm. Shape: Broadly rhomboidal. Apex: Aristate. Base: Cuneate. Margin: Entire. Texture and luster, upper and lower surfaces: Moderately tomentose; matte. Color, upper surface: Close to 186C to 186D; venation, close to 148A; pubescence, close to NN155A. Color, lower surface: Close to 186C to 186D; venation, close to 148B; pubescence, close to NN155A.

*Sepals*.—Quantity and arrangement: Five, fused into a campanulate tube. Length: About 6 mm. Width: About 0.75 mm. Shape: Lanceolate. Apex: Acute. Margin: Entire. Texture and luster, upper (inner) and lower (outer) surfaces: Densely pubescent; matte. Color: When opening and fully opened, upper (inner) surface: Close to 145C; venation, close to N187B to N187C; pubescence, close to NN155C to NN155D. When opening and fully opened, lower (outer) surface: Close to 145C; towards the apex tinged with close to between N187B and 200C; pubescence, close to NN155C to NN155D.

*Peduncles*.—Length: About 8.3 cm. Diameter: About 2 mm. Aspect: Mostly upright. Strength: Strong. Texture and luster: Densely tomentose; matte. Color: Close to 143C; towards the apex, tinged with close to N199B and N199C; pubescence, close to 157D.

*Reproductive organs*.—Stamens: Quantity per flower: Four. Filament length: About 0.5 mm. Filament color: Close to NN155D. Anther shape: Reniform. Anther length: About 0.5 mm. Anther color: Close to N92A. Pollen amount: Moderate. Pollen color: Close to 17B. Pistils: Quantity per flower: One. Pistil length: About 3.5 mm. Stigma shape: Club-shaped. Stigma color: Close to between N92A and 203D. Style length: About 3 mm. Style color: Close to NN157A. Ovary color: Close to 143A.

*Seeds and fruits*.—Seed and fruit production has not been observed on plants of the new *Lavandula*.

Disease & pest resistance: Plants of the new *Lavandula* have not been noted to be resistant to pathogens and pests common to *Lavandula* plants.

Garden performance: Plants of the new *Lavandula* have exhibited good tolerance to rain and wind and have been observed to tolerate high temperatures about 40° C. and to be hardy to USDA Hardiness Zone 7.

It is claimed:

1. A new and distinct *Lavandula* plant named 'Anouk Deluxe 1205' as illustrated and described.

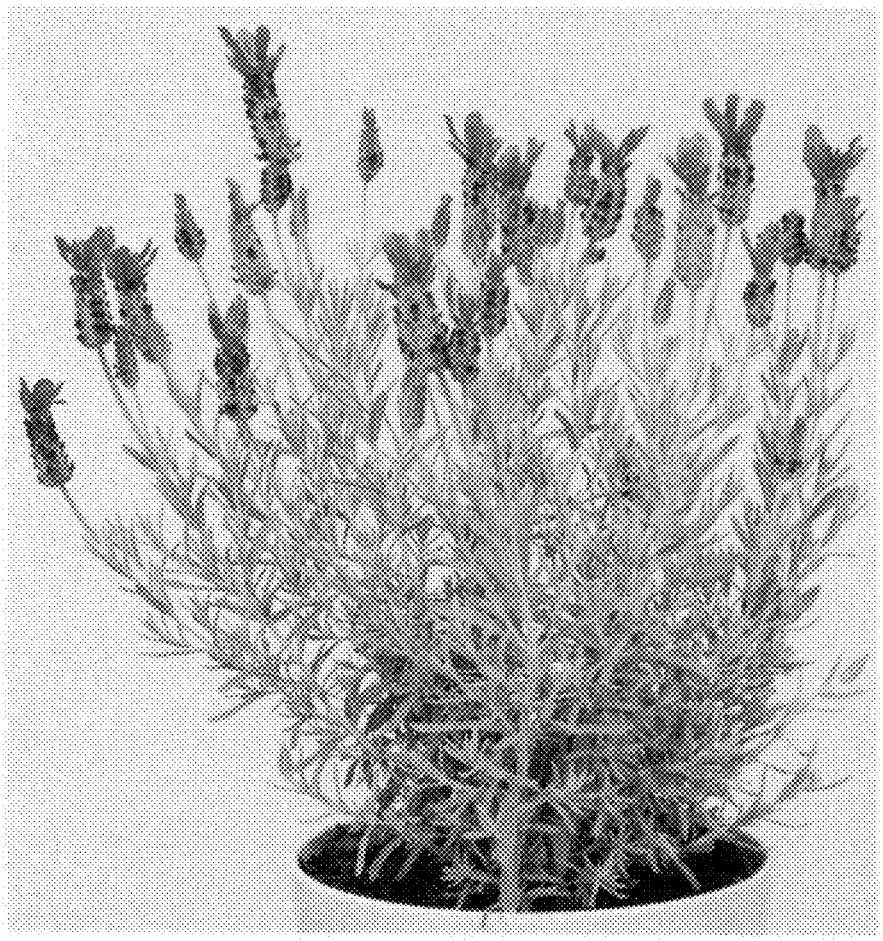

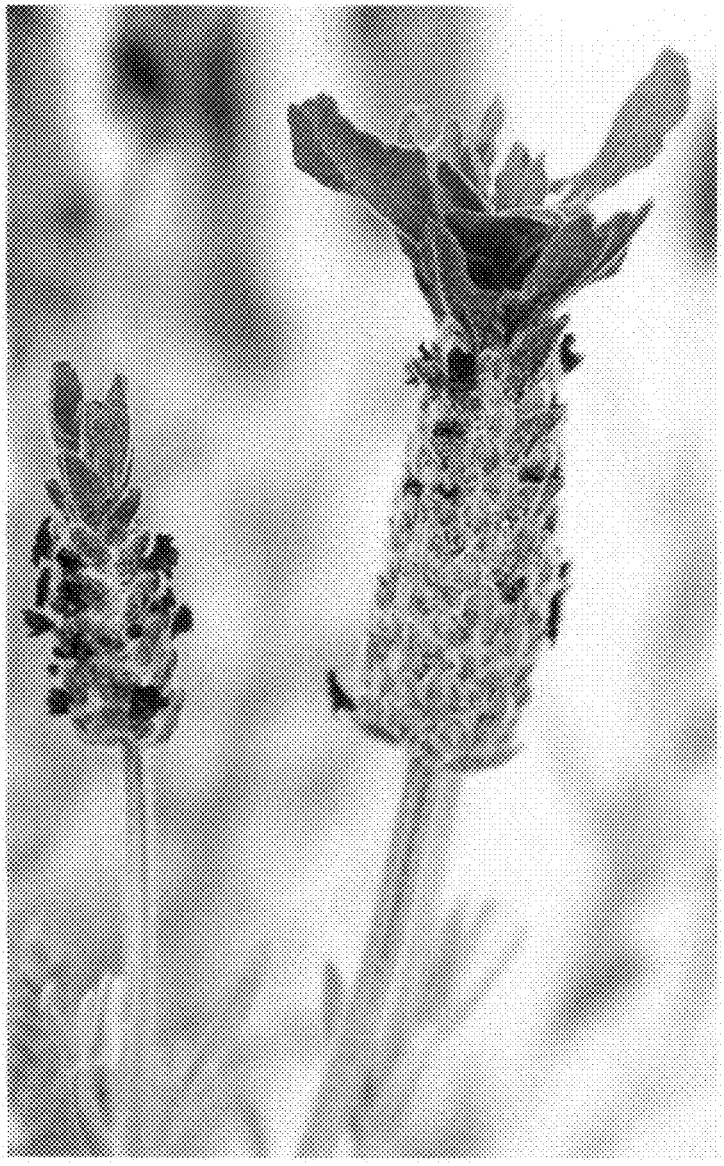

* * * * *